US006293966B1

United States Patent
Frantzen (12) United States Patent
(10) Patent No.: US 6,293,966 B1
(45) Date of Patent: *Sep. 25, 2001

(54) SURGICAL STENT FEATURING RADIOPAQUE MARKERS

(75) Inventor: John J. Frantzen, Copperopolis, CA (US)

(73) Assignee: Cook Incorporated, Bloomington, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/063,562

(22) Filed: Apr. 20, 1998

Related U.S. Application Data (63) Continuation of application No. 08/852,016, filed on May 6, 1997, now Pat. No. 5,741,327.

(51) Int. Cl.$^7$ ........................................................ A61F 2/06
(52) U.S. Cl. ........................ 623/1.15; 623/1.34; 606/198
(58) Field of Search .............................. 623/1, 12, 1.15, 623/1.34; 606/153, 191, 198

(56) References Cited

U.S. PATENT DOCUMENTS

| D. 380,266 | 6/1997 | Boatman et al. . |
| D. 380,831 | 7/1997 | Kavteladze et al. . |
| 4,704,126 | 11/1987 | Baswell et al. . |
| 4,858,264 | 8/1989 | Reinhart . |
| 4,936,057 | 6/1990 | Rhoades . |
| 5,104,404 | 4/1992 | Wolff . |
| 5,108,417 | 4/1992 | Sawyer . |
| 5,133,732 | 7/1992 | Wiktor . |
| 5,139,480 | 8/1992 | Hickle et al. . |
| 5,195,984 | 3/1993 | Schatz . |
| 5,199,226 | 4/1993 | Rose . |
| 5,242,399 | 9/1993 | Lau et al. . |
| 5,314,444 | 5/1994 | Gianturco . |
| 5,383,892 | 1/1995 | Cardon et al. . |
| 5,421,955 | 6/1995 | Lau et al. . |
| 5,423,849 | 6/1995 | Engelson et al. . |
| 5,425,739 | 6/1995 | Jessen . |
| 5,441,515 | 8/1995 | Khosravi et al. . |

(List continued on next page.)

FOREIGN PATENT DOCUMENTS

95302708.3   4/1995  (EP) .

*Primary Examiner*—Paul B. Prebilic
(74) *Attorney, Agent, or Firm*—Anton P. Ness; Richard J. Godlewski (57) ABSTRACT

Radiopaque marker elements for attachment to ends of a radially expandable surgical stent are disclosed. Each radiopaque marker element is homogeneously formed from a radiopaque material and attached through an attachment means to ends of the stent. The radiopaque marker elements enhance the visibility of the stent when the stent is viewed with a medical imaging device, such as a fluoroscope. The marker elements extend beyond ends of the stent. The marker elements are attached to the stent before radial expansion and are configured to radially expand along with the stent during surgical implantation thereof within a body lumen, such as an artery. The radiopaque marker elements can either be attached to an unmodified radially expandable surgical stent or to a prepped stent which includes receivers at ends of the stent particularly configured to attach to the radiopaque marker elements. The radiopaque marker elements include tabs which match a contour of the receivers so that secure attachment of the radiopaque marker elements to the receivers at the ends of the stent is provided.

20 Claims, 8 Drawing Sheets

U.S. PATENT DOCUMENTS

| | | |
|---|---|---|
| 5,443,477 | 8/1995 | Marin et al. . |
| 5,443,496 | 8/1995 | Schwartz et al. . |
| 5,449,373 | 9/1995 | Pinchasik et al. . |
| 5,485,667 | 1/1996 | Kleshinski . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |
| 5,514,154 | 5/1996 | Lau et al. . |
| 5,522,882 | 6/1996 | Gaterud et al. . |
| 5,531,741 | 7/1996 | Barbacci . |
| 5,545,210 | 8/1996 | Hess et al. . |
| 5,549,662 | 8/1996 | Fordenbacher . |
| 5,549,663 | 8/1996 | Cottone . |
| 5,554,181 | 9/1996 | Das . |
| 5,562,641 | 10/1996 | Flomenblit et al. . |
| 5,562,728 | 10/1996 | Lazarus et al. . |
| 5,569,295 | 10/1996 | Lam . |
| 5,578,149 | 11/1996 | DeScheerder et al. . |
| 5,591,195 | 1/1997 | Taheri et al. . |
| 5,591,197 | 1/1997 | Orth et al. . |
| 5,591,223 | 1/1997 | Lock et al. . |
| 5,591,226 | 1/1997 | Trerotola et al. . |
| 5,591,230 | 1/1997 | Horn et al. . |
| 5,603,721 | 2/1997 | Lau et al. . |
| 5,605,530 | 2/1997 | Fischell et al. . |
| 5,607,442 | 3/1997 | Fischell et al. . |
| 5,607,445 | 3/1997 | Summers . |
| 5,618,299 | 4/1997 | Khosravi et al. . |
| 5,624,411 | 4/1997 | Tuch . |
| 5,630,840 | 5/1997 | Mayer . |
| 5,632,760 | 5/1997 | Sheiban et al. . |
| 5,632,763 | 5/1997 | Glastra . |
| 5,632,771 | 5/1997 | Boatman et al. . |
| 5,634,941 | 6/1997 | Winston et al. . |
| 5,636,641 | 6/1997 | Fariabi . |
| 5,637,113 | 6/1997 | Tartaglia et al. . |
| 5,697,971 | 12/1997 | Fischell et al. . |
| 5,725,549 * | 3/1998 | Lam ................................. 623/1.15 |
| 5,741,327 * | 4/1998 | Frontzen ............................... 623/12 |
| 5,746,691 | 5/1998 | Frantzen . |
| 5,824,042 * | 10/1998 | Lombardi et al. ...................... 623/1 |
| 5,993,481 * | 11/1999 | Marcade et al. ........................ 623/1 |
| 6,174,330 * | 1/2001 | Stinson ............................. 623/1.34 |

* cited by examiner

SURGICAL STENT FEATURING RADIOPAQUE MARKERS

CROSS-REFERENCE TO RELATED APPLICATIONS

This application is a continuation of U.S. application Ser. No. 08/852,016, filed on May 6, 1997, now U.S. Pat. No. 5,741,327.

FIELD OF THE INVENTION

The following invention relates to stents for implantation into a body lumen, such as an artery, which are radially expandable. More specifically, this invention relates to radially expandable surgical stents which are provided with radiopaque markers thereon to enhance their visibility when viewed with an imaging device such as a fluoroscope.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance in various different particular circumstances. For instance, the United States patents to Lau (U.S. Pat. Nos. 5,514,154, 5,421,955, and 5,242,399), Baracci (U.S. Pat. No. 5,531,741), Gaterud (U.S. Pat. No. 5,522,882), Gianturco (U.S. Pat. Nos. 5,507, 771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

One problem encountered in the use of radially expandable surgical stents is the difficulty in precisely determining the position of the stent both before, during and after it is implanted and expanded. Typically, stents are formed from stainless steel or a nickel titanium alloy. These materials are not readily perceptible when medical imaging devices, such as fluoroscopes are used to view the site where the stent has been implanted. To enhance the radiopacity of surgical stents, it is known in the prior art to provide a radiopaque marker on the stent which is clearly identifiable when a fluoroscope or other imaging device is used. Such radiopaque stents taught in the prior art have suffered from a number of drawbacks. For instance, many radiopaque markers restrict the ability of the stent to expand radially, protrude from the surface of the stent in a potentially harmful manner, fail to provide a complete outline of the extent of the stent, or illuminate so brightly on an imaging device that fine details such as blood vessels and other bodily structures are obscured in the images obtained.

One such radiopaque marker stent is the subject of European Patent Application No. 95302708.3 published on Nov. 2, 1995. The radiopaque stent markers identified in this European patent application utilize plating techniques to plate a band of radiopaque material to portions of the radially expandable stent. The radiopaque stent markers disclosed in this European patent application significantly enlarge the thicknesses of the elements adjacent where the plating occurs, making this technique significantly less effective on stents sized for implantation in smaller body lumens. If a lesser plating thickness is utilized, insufficient radiopaque material is added to provide the desired radiopacity. Other drawbacks of the radiopaque stent markers of this European patent application include that the plating material can become detached from the stent, especially when the plating material is gold and the stent is made of stainless steel. Also, such plated stents must be masked on both outer and inner surfaces. The masking procedure is difficult to accurately perform, especially on inner surfaces of stents with small diameters.

Accordingly, a need exists for a radially expandable stent featuring radiopaque markers which can be utilized on stents of all different sizes, does not interfere with the expansion of the stent and provides a clear image on a fluoroscope or other medical imaging device. Such a stent with radiopaque markers should additionally be configured in a manner facilitating its manufacture using known manufacturing techniques and commonly utilized implantation materials.

SUMMARY OF THE INVENTION

This invention provides radiopaque marker elements for attachment to radially expandable surgical stents. Separate marker elements are attached to ends of the stent which allow the ends of the stent to be readily viewable by a fluoroscope or other imaging device. The marker elements are formed of a homogeneous material having radiopaque characteristics, rather than merely having a surface of radiopaque material overlying other non-radiopaque elements of the stent.

Each marker element is mechanically attached to an end of the stent with an axial center of the marker element coextensive with a central axis of the stent. The marker element is configured to be radially expandable in a manner similar to the radial expansion of the stent itself. Thus, the presence of the marker element adjacent an end or ends of the stent does not in any way inhibit the radial expansion of the stent within a body lumen during use. The marker elements are attached to the ends of the stent in positions beyond the ends of the stent so that when a marker element is attached to both ends of the stent, the stent can be viewed with an imaging device, such as a fluoroscope, and the maximum extent and precise position of the stent can be accurately determined. The marker elements can either be circumferentially continuous, completely circumscribing the central axis of the stent, or discontinuous with a series of disconnected marker elements secured to the ends of the stent at separate positions thereon.

In a preferred form of the invention, the marker elements have a circumferential contour which mirrors a contour of other circumferential elements forming the cylindrical radially expandable stent. In this way, such circumferential marker elements provide a geometric structure and expansion characteristics to the stent which mirror those of other portions of the stent and do not alter performance of the stent.

The marker elements can either be located directly adjacent the ends of the stent in a manner only slightly increasing a length of the stent or the marker elements can be spaced from the adjacent portions of the stent in a manner causing the marker elements to enhance somewhat the overall length of the stent. With the radiopaque marker elements in place attached to the ends of the stent, the location and orientation of the stent can be precisely determined both before, during and after implantation and radial expansion of the surgical stent within the body lumen.

OBJECTS OF INVENTION

Accordingly, a primary object of the present invention is to provide a radially expandable surgical stent which features radiopaque marker elements attached thereto which enhance visibility of the stent when viewed through a fluoroscope or other imaging device.

Another object of the present invention is to provide a radially expandable surgical stent with radiopaque marker elements that do not inhibit radial expansion and support of a body lumen by having the radiopaque markers included thereon.

Another object of the present invention is to provide radiopaque marker elements for a surgical stent which attach to ends of the stent and which are homogeneously formed from a radiopaque material.

Another object of the present invention is to provide radiopaque marker elements for a surgical stent which completely circumscribe a central axis of the stent.

Another object of the present invention is to provide a radiopaque marker element attachable to a surgical stent which can itself be radially expanded when the surgical stent is radially expanded.

Another object of the present invention is to provide a radiopaque marker for surgical stents formed from both stainless steel and nickel titanium.

Another object of the present invention is to provide a radiopaque stent which is distinctly visible when viewed with an imaging device, such as a fluoroscope, but does not obscure other structures located adjacent to the radiopaque markers.

Another object of the present invention is to provide a joint for attaching radiopaque marker elements to ends of a radially expandable surgical stent.

Other further objects of the present invention will become apparent from a careful reading of the detailed description of the preferred embodiments, the claims and the drawing figures included herein.

DESCRIPTION OF THE PREFERRED EMBODIMENTS

Figure 1:
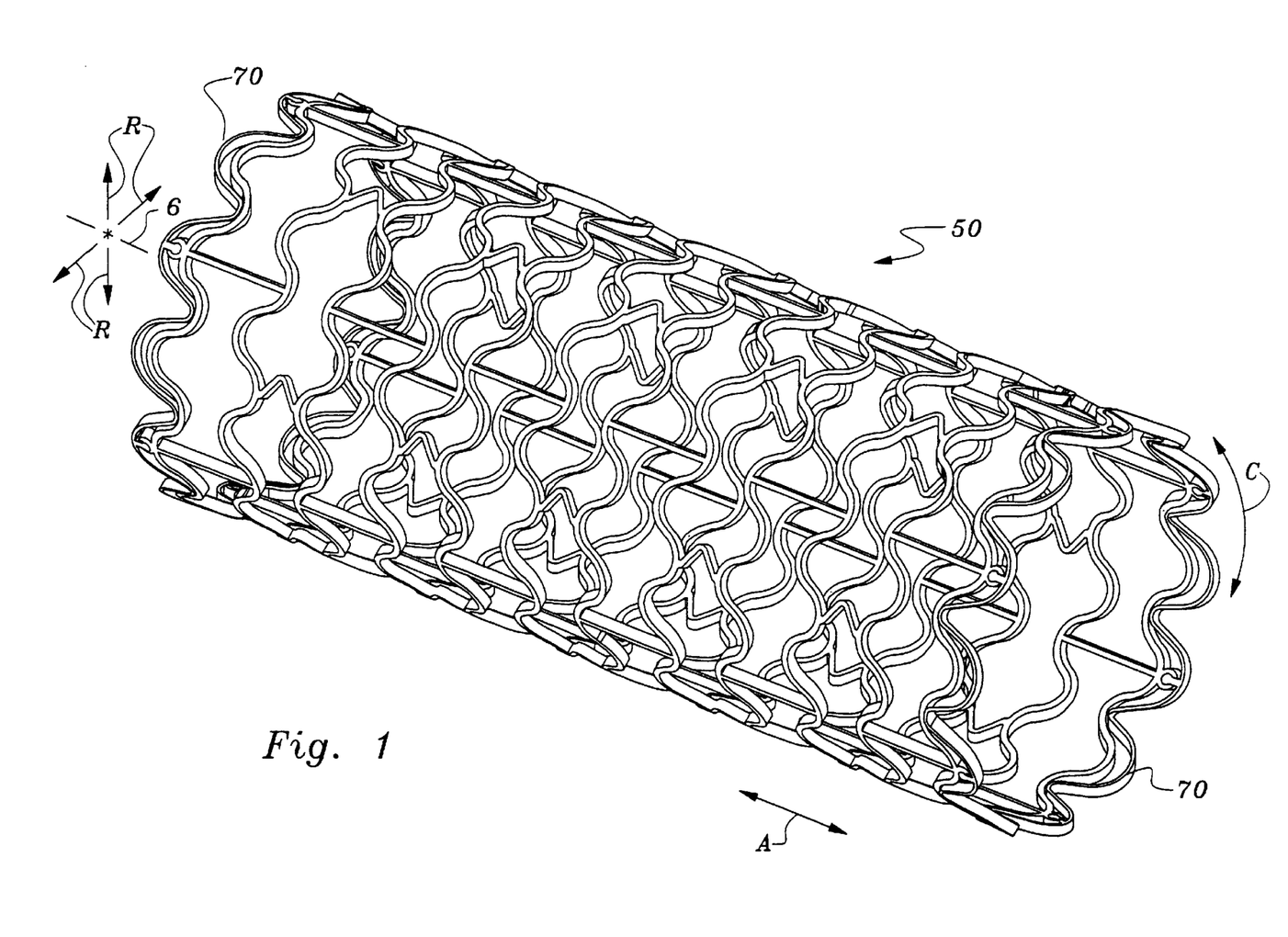
FIG. 1 is a perspective view of a radially expandable surgical stent with a circumferential marker element attached to each end of the stent.
Figure 2:
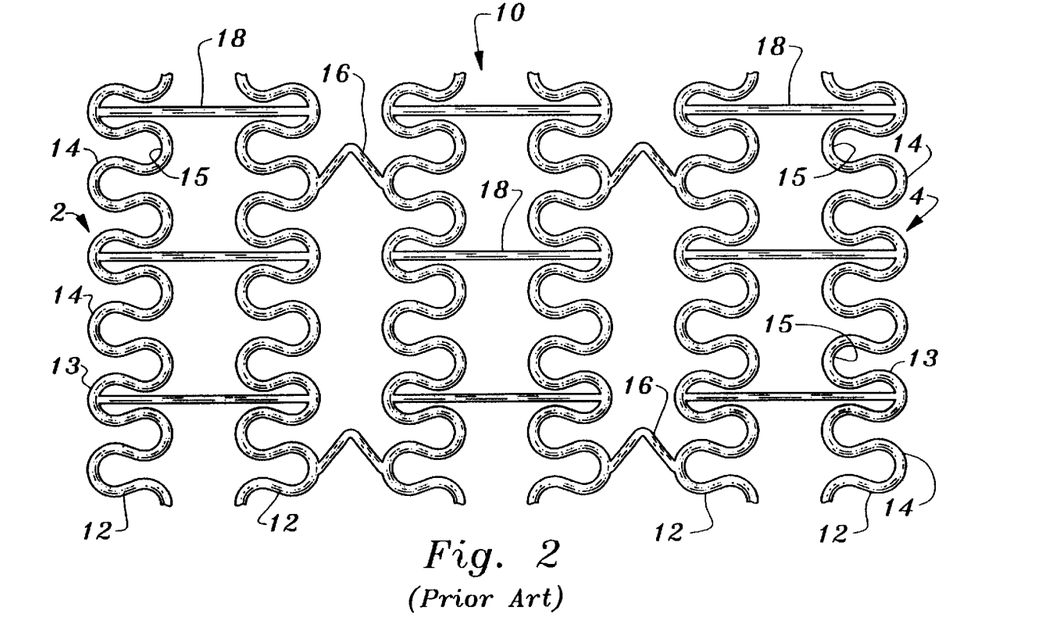
FIG. 2 is a cylindrical projection of a portion of a prior art radially expandable surgical stent before any radiopaque markers are attached thereto.
Figure 3:
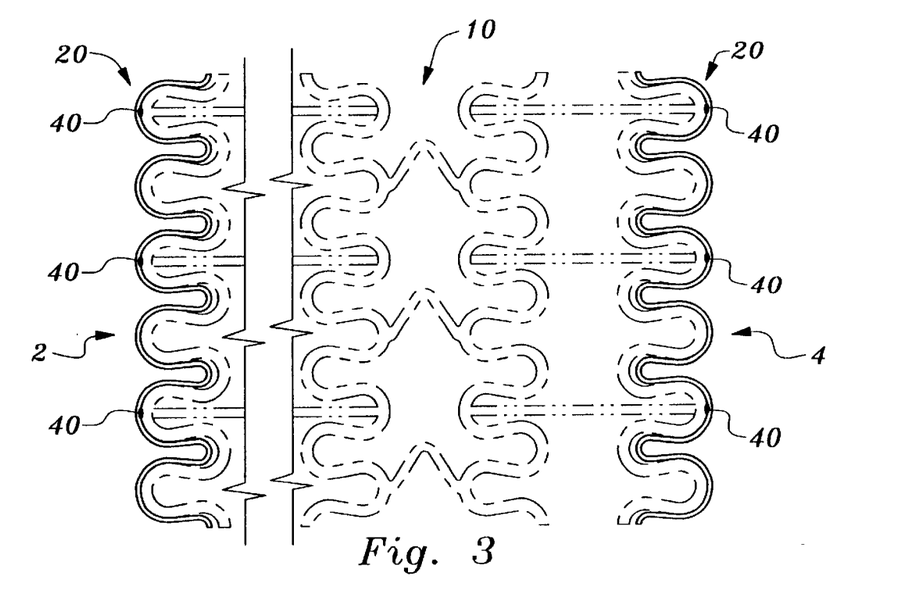
FIG. 3 is a cylindrical projection of a portion of that which is shown in FIG. 2 with circumferential marker elements attached to each end of the stent. The stent is shown in broken lines and the circumferential marker elements are shown with solid lines, indicating the relative visibility and obscurity of the circumferential marker elements and the stent such as would appear when the stent and marker elements are viewed with a medical imaging device.

With reference to the drawing figures, wherein like reference numerals represent like parts throughout the various different figures, reference numeral 10 is directed to a prior art radially expandable surgical stent frame such as a wire frame to which a circumferential marker member or element 20 can be attached according to this invention (FIG. 3). Circumferential marker elements 20 have a preselected size and shape corresponding to an associated portion of the stent frame before being attached thereto, and are attached to the stent 10 adjacent a first end 2 and a second end 4 of the stent 10. When the stent 10 with marker elements 20 is viewed with a medical imaging device, such as a fluoroscope, the positions of the ends 2, 4 of the stent are identified by the presence of the marker elements 20 adjacent the ends 2, 4. A position and orientation of the stent 10 can thus be more readily determined when using a medical imaging device. While FIGS. 2–17 and 19 are two-dimensional cylindrical projections of various elements of this invention, it should be understood that these elements are in fact three-dimensional in nature, such as depicted in FIG. 1. The invention is shown in two dimensions for convenience in understanding the structure of the various elements of this invention.

In essence, and with particular reference to FIGS. 1–6, the basic configuration of the stent 10 and circumferential marker element 20 attached thereto is described. The stent 10 (FIG. 2) is formed from a series of circumferential elements 12 oriented in planes substantially parallel to each other with each circumferential element 12 circumscribing a cylindrical contour of the stent 10. The cylindrical contour of the stent 10 is generally analogous to that exhibited in FIG. 1 for the prepped stent 50 described in detail below. Each circumferential element 12 has an undulating pattern including a series of prominences 14 and recesses 15. These prominences 14 and recesses 15 allow the circumferential elements 12 to be radially expanded, causing the stent 10 to be enlarged from a smaller cylindrical diameter to a larger cylindrical diameter (such as long arrow R of FIG. 1). Angled axial elements 16 and linear axial elements 18 tie adjacent circumferential elements 12 to each other.

Two circumferential marker elements 20 (FIG. 5) are provided, one adjacent the first end 2 (FIG. 3) of the stent 10 and the other adjacent the second end 4 of the stent 10. Each circumferential marker element 20 has an undulating contour including a series of alternating crests 22 and troughs 24. The circumferential marker elements 20 can thus also be radially expanded in a manner analogous to that of the circumferential elements 12.

Each circumferential marker element 20 is attached to either the first end 2 or the second end 4. One means for attaching the circumferential marker elements 20 to the stent 10 is to provide a braze point 40 (FIG. 3) where the circumferential marker elements 20 are brazed to the stent 10. The braze point 40 is repeated at sufficient locations around the circumference of each end 2, 4 to ensure that each circumferential marker element 20 remains securely attached to the first end 2 and second end 4 of the stent 10. The stent 10 can then be surgically implanted into a body lumen and radially expanded with the circumferential marker elements 20 securely in place adjacent the ends 2, 4 of the stent 10 and providing enhanced visibility for the ends 2, 4 of the stent 10 when viewed through a medical imaging device, such as a fluoroscope.

More specifically and with particular reference to FIGS. 2–6, details of a first embodiment is described featuring circumferential marker elements 20 attached to a prior art unmodified stent 10. In this embodiment, the stent 10 does not itself require any modifications or alteration in configuration. Rather, the circumferential marker elements 20 are merely attached to the ends 2, 4 (FIG. 3) of the stent 10 through utilization of an appropriate attachment means.

The stent 10 can be any of a variety of different configurations. However, the circumferential marker elements 20 of this embodiment, being radially expandable, are particularly well suited for attachment to stents 10 which feature the ability to expand radially after implantation to securely position the stent adjacent interior walls of a body lumen, such as an artery. Additionally, the circumferential marker elements 20 are particularly well suited for attachment to flexible radially expandable stents such as the prior art stent 10 shown in detail in FIG. 2.

This stent 10 includes a series of circumferential elements 12 oriented in adjacent parallel planes from the first end 2 of the stent 10 to the second end 4 of the stent 10. Each of the circumferential elements 12 are aligned symmetrically with a constant radius away from a common central axis 6 passing through a center of the cylindrical contour of the stent 10 (see FIG. 1 where the prepped stent 50, having a closely analogous configuration to that of the stent 10, reveals the position of the central axis 6).

Each circumferential element 12 has a wave-like undulating pattern which includes a series of alternating prominences 14 and recesses 15. Each circumferential element 12 is tied to adjacent circumferential elements by either angled axial elements 16 or linear axial elements 18. Taken together, the elements 12, 16, 18 form the prior art stent 10. End surfaces 13 define outward facing surfaces of the circumferential elements 12 adjacent the first end 2 and second end 4 of the stent 10. The end surfaces 13 preferably provide the location for attachment of the circumferential marker elements 20. Each circumferential marker element 20 is generally circular in form with an axial center aligned with the central axis of the stent 10. The circumferential marker element 20 has a radius matching the radius of the stent 10. Thus, the circumferential marker elements 20 reside in a cylindrical region along with the stent 10.

Each circumferential marker element 20 (FIG. 5) preferably has a wave-like undulating contour. This marker contour is analogous to an end contour of the first end 2 and second end 4 of the stent 10, allowing the marker elements 20 to be oriented adjacent the end surfaces 13 and providing multiple locations for attachment of the circumferential marker elements 20 to the end surface 13 of the stent 10.

Preferably the marker contour of the circumferential marker element 20 includes a series of alternating crests 22 and troughs 24 somewhat analogous to the prominences 14 and recesses 15 of the circumferential elements 12 of the stent 10. Each circumferential marker element 20 has an adjacent side 26 facing the end surface 13 of either the first end 2 or second end 4 and an opposite side 28 opposite the adjacent side 26. For convenience, each crest 22 is defined as the location on the circumferential marker element 20 where the opposite side 28 is convex and extends a maximum distance away from a plane along which the circumferential marker element 20 is aligned. Each trough 24 defines a location where the adjacent side 26 extends a maximum distance away from the plane in which the marker element 20 is oriented.

The crests 22 and troughs 24 are preferably not symmetrical on the circumferential marker element 20. Rather, each crest 22 features a broad curve 30 having a relatively large radius of curvature. Each trough 24 preferably exhibits a tight curve 34 having a radius of curvature smaller than that of the broad curve 30. Each tight curve 34 is joined to adjacent broad curves 30 by inflection regions 32 there between. With this asymmetrical crest 22 and trough 24 configuration for each circumferential marker element 20, the crest can overlie the end surface 13 of a circumferential element 12 adjacent a prominence 14 and the trough 24 can be nested within a recess 15 in the end surface 13 of the circumferential element 12.

Preferably, the broad curve 30 and tight curve 34 are configured to closely follow the end surface 13 of the circumferential element 12 adjacent thereto (FIG. 6) but with each tight curve 34 of each trough 24 preferably slightly short of the contact with the end surface 13 within the recess 15. Radial expansion of the circumferential elements 12 adjacent the first end 2 and second end 4 of the stent 10 is thus not inhibited by positioning of circumferential marker elements 20 adjacent the ends 2, 4.

Figure 4:
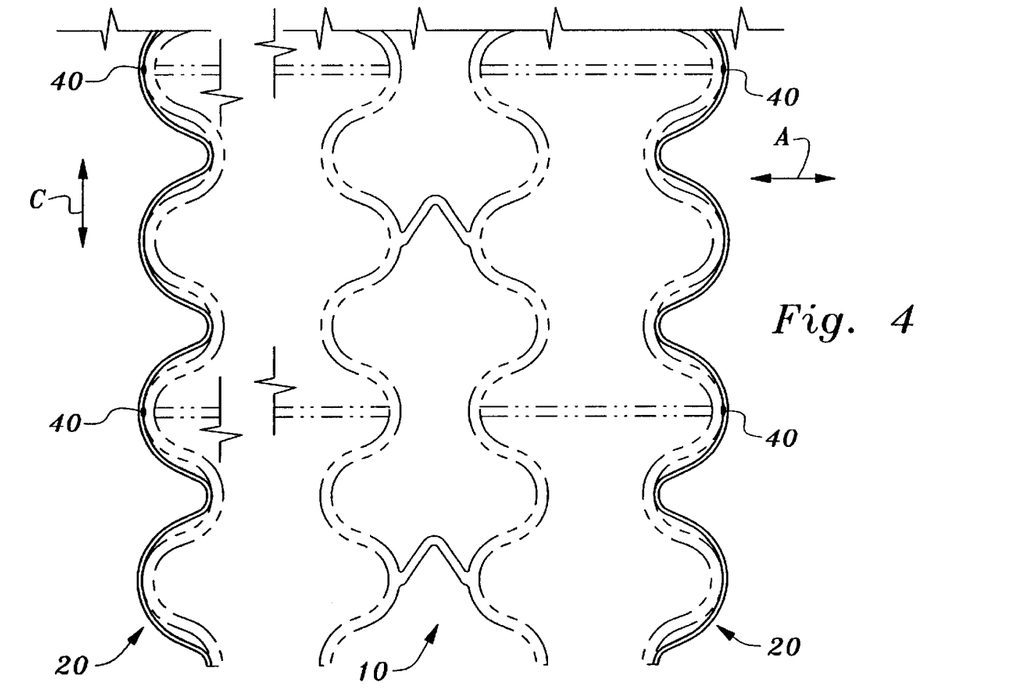
FIG. 4 is a cylindrical projection of a portion of that which is shown in FIG. 3 after radial expansion of the stent and the circumferential marker elements attached to the stent.
Figure 5:
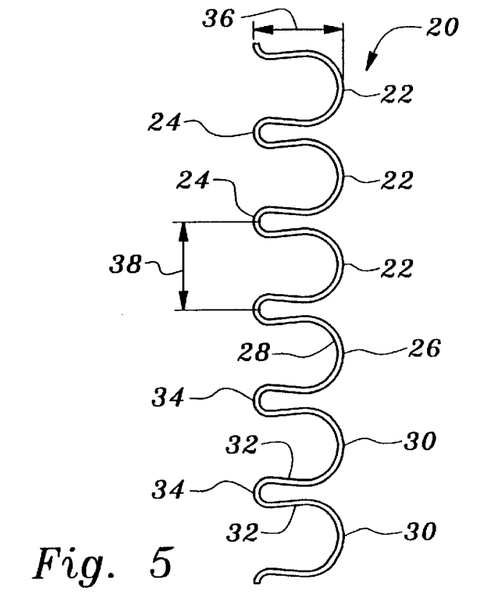
FIG. 5 is a cylindrical projection of one of the circumferential marker elements of this invention before its attachment to a stent.
Figure 6:
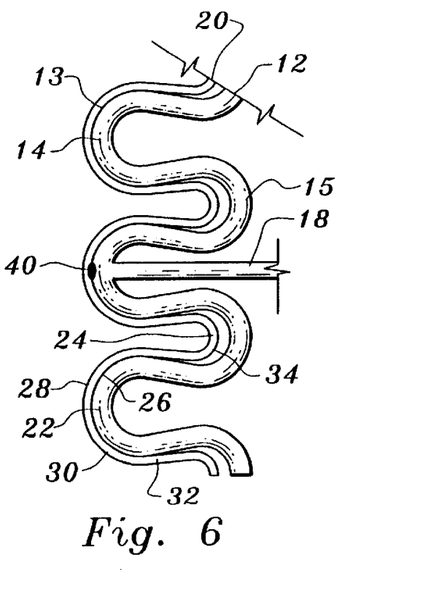
FIG. 6 is a cylindrical projection of a portion of that which is shown in FIG. 3 revealing details of the attachment of one of the circumferential marker elements to an end of the stent using a brazing technique.

Each circumferential marker element has an amplitude 36 and wave length 38 (FIG. 5) which allow the circumferential marker elements 20 to match the contour of the end surface 13 of a circumferential element 12 adjacent the first end 2 or second end 4 of the stent 10. When the stent 10 is radially expanded, the amplitude 36 of the circumferential marker elements 20 attached to the stent 10 can be decreased and the wave length 38 and overall circumferential length (along arrow C of FIG. 4) of the circumferential marker elements 20 can be increased. The circumferential marker elements 20 are thus allowed to radially expand along with the stent 10 (such as along arrow R of FIG. 1 showing radial expansion of the prepped stent 50 described below), without altering the performance of the stent 10 in any manner (FIGS. 3 and 4). The undulating marker contour of the circumferential marker element 20 and the flexibility of the marker material provides one form of radial expansion means for the circumferential marker elements 20.

When the prior art stent 10 is completely unmodified various different means for attachment and joining of the circumferential marker elements 20 to the first end 2 and second end 4 of the stent 10 can be utilized. Preferably, when the stent 10 itself is unmodified, the attachment means is a series of braze points 40 where an appropriate fluxing material can be interposed between the end surface 14 and the adjacent side 26 of one of the marker elements 20, causing the marker element 20 to be brazed into fixed attachment with the stent 10.

For example, when the circumferential marker element 20 is formed from gold or a gold alloy and the circumferential elements 12 forming the stent 10 are formed from stainless steel, gold can be used as a fluxing material and applied at the braze point 40 to secure the circumferential marker element 20 to the stent 10. Preferably, braze points 40 are provided around a circumference of the cylindrical contour of the stent 10. If the wave length of the marker elements 20 is one-sixth of a circumference of the stent 10 preferably three brazed points 40 are provided at broad curves 30 in each circumferential marker element 20.

When the stent 10 is formed from a stent material such as a nickel titanium alloy, brazing is not readily accomplished due to oxide layers forming on the surface of the nickel titanium stent 10. To allow the marker element 20 to be more effectively brazed to a nickel titanium stent, one appropriate method is to heat the nickel titanium alloy in a vacuum or reduced oxygen environment and then sputter gold onto the surface of the nickel titanium stent 10. Once the gold has been sputtered onto the nickel titanium, gold can be used as a fluxing material to braze the marker elements 20 to the stent 10. While gold has been used as an example as the fluxing material and the marker material forming the circumferential marker elements 20, other acceptable materials can be used. Such materials include silver and silver alloys, platinum and platinum alloys and many other materials known in the art which exhibit radiopacity when viewed through a medical imaging device such as a fluoroscope. The circumferential marker element 20 is preferably homogeneous throughout. Specifically, the same metal or metal alloy forms all portions of the element 20 along its length and from its surface down to its core.

Other means for attaching the circumferential marker elements 20 to the ends 2, 4 of the stent 10 can be utilized including epoxies, mechanical fasteners, weaving of the circumferential marker elements 20 into the stent 10 and other known attachment techniques.

As an alternative to utilization of an unmodified prior art stent 10 for attachment with circumferential marker elements 20, a prepped stent 50 (FIGS. 1 and 7–11) can be utilized along with locking marker elements 70 particularly configured to interface with and attach to the prepped stent 50. Specifically, the prepped stent 50 preferably has an identical pattern to that exhibited by the prior art stent 10 except that end surfaces 53 of the prepped stent 50 feature receivers 60 extending from the end surface 53. Thus the prepped stent 50 has ends with a wave-like undulating contour including a series of prominences 54 and recesses 55 in an alternating pattern. Angled axial elements 56 and linear axial elements 58 tie adjacent circumferential elements 59 to each other. Every other prominence 54 of the prepped stent 50 preferably includes a receiver 60 extending therefrom. Each receiver 60 is somewhat "C-shaped" with a rounded space 62 at a center thereof which can be accessed through a gap 63 between a first finger 64 and a second finger 67. The first finger 64 extends from a base 65 adjacent the prominence 54 to a tip 66 opposite the base 65. The second finger 67 similarly includes a base 68 adjacent the prominence 54 and a tip 69 opposite the base 68. Each finger 64, 67 curves slightly to form the rounded space 62 and the gap 63 extending into the rounded space 62. The rounded space 62 has a width which is greater than a width of the gap 63. The receiver 60 is preferably formed along with other portions of the prepped stent 50 from similar materials as those forming the prepped stent 50. The receivers 60 are thus an integral part of each prepped stent 50.

Each locking marker element 70 (FIG. 10) is preferably similar in form to the circumferential marker elements 20 except that the locking marker elements 70 are particularly configured to interface with the receivers 60 of the prepped stent 50 for secure attachment of the locking marker elements 70 adjacent ends of the prepped stent 50. Thus, each locking marker element 70 includes a wave-like undulating pattern with a series of crests 72, 73 and troughs 74. The crests 72, 73 include high crests 72 and low crests 73 interposed between each high crest 72. Each trough 74 preferably extends a similar distance away from a central plane in which the locking marker element 70 is oriented.

Each locking marker element 70 includes an adjacent side 76 configured to be located adjacent the end surface 53 of the prepped stent 50 and an opposite side 78 opposite the adjacent side 76. The high crest 72 is sized to accommodate the location of the receiver 60 of the prepped stent 50 therein and the low crest 73 is sized to overlie the end surface 53 of the prepped stent 50 at prominences 54 where no receiver 60 is located.

Each high crest 72 is formed by a high broad curve 80 in the locking marker element 70. Each low crest 73 is formed by a low broad curve 81 in the locking marker element 70. Each trough 74 is formed by a tight curve 84. A long inflection region 82 extends between each high broad curve 80 and each tight curve 84 and a short inflection region 83 is located between each low broad curve 81 and each tight curve 84. As can be seen, particularly in FIG. 11, the tight curves 84 allow the locking marker element 70 to remain closely adjacent the end surface 53 of the prepped stent 50 within each recess 55 in the prepped stent 50. The high broad curve 80 and low broad curve 81 alternatively overlie prominences 54 and the prepped stent 50 which have receivers 60 thereon and prominences 54 in the prepped stent 50 which do not have receivers 60 located thereon.

Figure 8:
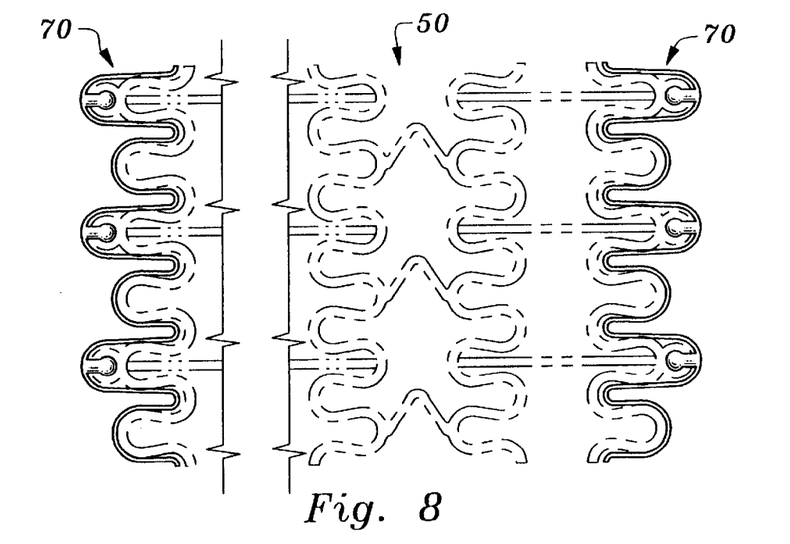
FIG. 8 is a cylindrical projection of that which is shown in FIG. 7 with a locking marker element attached to each end of the stent. Portions of the stent formed with non-radiopaque material are shown with broken lines representing how the appearance of such portions would be diminished when compared to the radiopaque portions of the stent when the stent is viewed with an imaging device.
Figure 9:
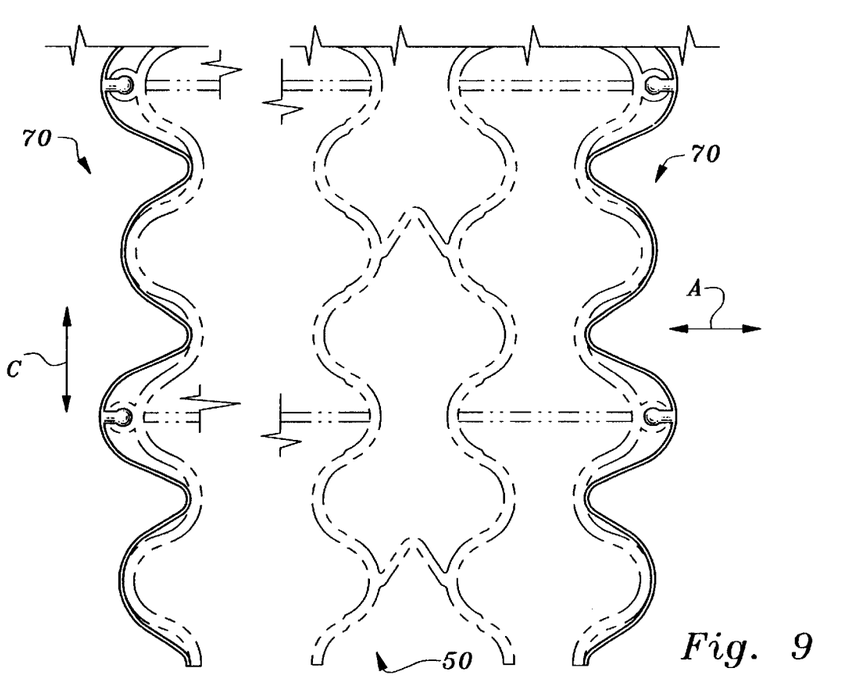
FIG. 9 is a cylindrical projection of a portion of that which is shown in FIG. 8 revealing how the stent of FIG. 8 would appear upon radial expansion thereof.
Figure 10:
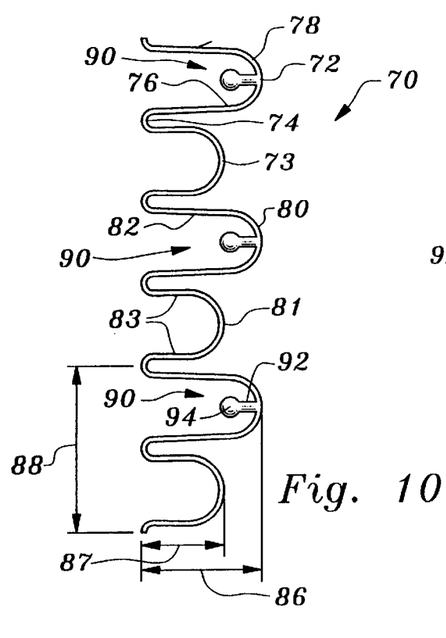
FIG. 10 is a cylindrical projection of the locking marker element before its attachment to the stent of FIG. 7.
Figure 11:
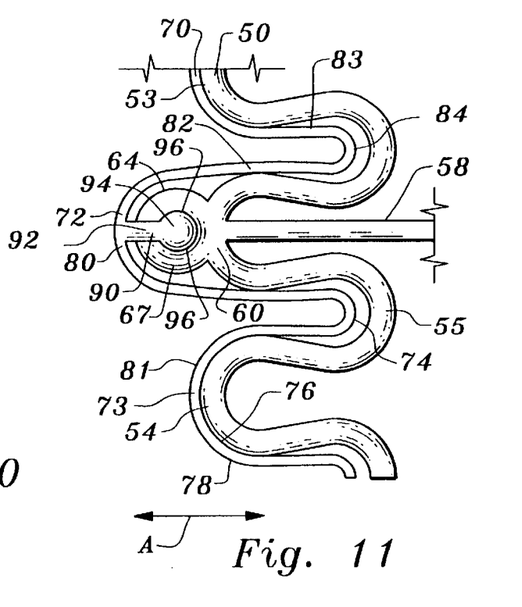
FIG. 11 is a cylindrical projection of a portion of that which is shown in FIG. 8 revealing details of the attachment means between the locking marker element of FIG. 10 and the prepped stent of FIG. 7.

The locking marker element 70 has a high amplitude 86 defining an axial distance between the trough 74 and the high crest 72 and a low amplitude 87 defining the axial distance between the trough 74 and the low crest 73. The locking marker element 70 has a wave length 88 defined by a distance between each complete cycle including both a low crest 73 and a high crest 72. As with the circumferential marker element 20 and circumferential elements 12 of the stent 10, both the prepped stent 50 and locking marker element 70 can have their amplitudes reduced and their wave lengths increased such that they experience radial expansion when desired during the stent implantation process (FIGS. 8 and 9).

Each high crest 72 of the locking marker element 70 includes an inside tab 90 extending axially away from the adjacent side 76 of the locking marker element 70. The inside tab 90 includes a neck 92 extending away from the adjacent side 76 within the high crest 72 to a knob 94 at an end of the neck 92 opposite the adjacent side 76. The knob 94 has a width greater than a width of the neck 92. Preferably, the neck 92 has a width similar to a width of the gap 63 of the receiver 60 and the knob 94 has a width similar to a width of the rounded space 62 in the receiver 60.

Additionally, each inside tab 90 is positioned on the adjacent side 76 of the high crest 72 in a position allowing the inside tab 90 to be located within the rounded space 62 and gap 63 of the receiver 60. While the knob 94 is preferably shown as round and matching or complementary to the rounded space 62, various different matching patterns for the knob 94 and rounded space 62 could be successfully utilized. Other shapes for the knob 94 and rounded space 62 could alternatively be utilized, so long as the knob 94 can be oriented within the rounded space 62.

A fusion line 96 defines an interface along the edge of the knob 94 and neck 92 and along the edge of the rounded space 62 and gap 63 where the inside tab 90 is directly adjacent the receiver 60. This fusion line 96 can be manipulated through various different techniques to attach the inside tab 90 to the receiver 60. For instance, a laser can be directed at the knob 94 causing the knob 94 of the inside tab 90 to melt along with adjacent portions of the rounded space 62 and gap 63 and resolidify with the inside tab 90 and receiver 60 securely locked together across the fusion line 96.

The receiver 60 and inside tab 90 thus provide one form of attachment means between marker elements such as the circumferential marker element 20 and the locking marker element 70 to stents such as the stent 10 and the prepped stent 50. Alternatively, brazing and or sputtering techniques can be utilized to secure the inside tab 90 to the receiver 60. It is also conceivable that a mere mechanical locking of each inside tab 90 within each receiver 60 could be utilized to attach the locking marker element 70 to ends of the prepped stent 50. For instance, the knob 94 of the tab 90 could be pushed between the fingers 64, 67 forming the receiver 60 along the gap 63 until the knob 94 snaps securely into the rounded space 62. As shown in FIGS. 8 and 9, the locking marker element 70 can expand circumferentially, along arrow C, along with the circumferential elements 59 forming the prepped stent 50. The locking marker elements 70 thus enhance a visibility of ends of the prepped stent 50 when viewed through a medical imaging device without hampering radial expansion of the prepped stent 50.

Figure 7:
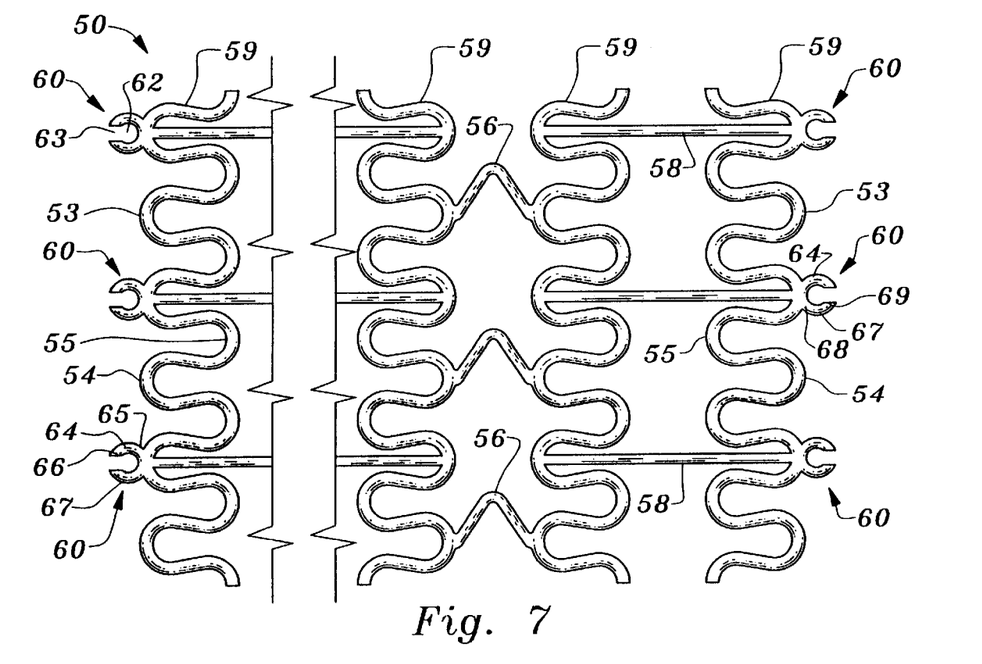
FIG. 7 is a cylindrical projection of a portion of a surgical stent which has been modified to include one half of an attachment means which facilitates secure attachment of marker elements to ends of the stent.

With reference to FIGS. 12–15, details of an extended marker element 100 are provided. The extended marker element 100 is interchangeable with the locking marker element 70 on the prepped stent 50 and is configured to be attached through an appropriate attachment means such as those disclosed herein, to the prepped stent 50 (FIG. 7). The extended marker element 100 does not remain directly adjacent the end surfaces 53 of the prepped stent 50 as does the locking marker element 70, or analogously the circumferential marker elements 20 to the stent 10. Rather, the extended marker element 100 extends significantly beyond ends of the prepped stent 50 enhancing an axial length (along arrow A) of the prepped stent 50 and extended marker element 100 combination.

Each extended marker element 100 has a wave-like undulating contour similar to the circumferential elements 59 of the prepped stent 50. In this way, radial expansion of the extended marker element 100 is very closely analogous to radial expansion of the prepped stent 50. The extended marker elements 100 can either be utilized with a prepped stent 50 having fewer circumferential elements 59, so that an overall axial length of the prepped stent 50 with extended marker elements 100 is not altered or the extended marker elements 100 can be utilized to increase an overall axial length of the prepped stent 50.

Each extended marker element 100 includes a series of alternating crests 102 and troughs 104 and has an adjacent side 106 and an opposite side 108 opposite the adjacent side 106. An inflection region 112 is interposed between each adjacent crest 102 and trough 104. Unlike the circumferential marker element 20 and locking marker element 70, the crests 102 and troughs 104 of the extended marker element 100 are similar in curvature like the contour of the circumferential elements 59 of the prepped stent 50.

A series of outside tabs 120 are located on the adjacent side 106 of the extended marker element 100 at crests 102 thereof. Each outside tab 120 includes a neck 122 and knob 124 similar in contour to the neck 92 and knob 94 of the inside tab 90 of the locking marker element 70. However, each outside tab 120 is located extending axially, along arrow A, away from a crest 102, on the adjacent side 106 of the extended marker element 100, rather than the orientation of the inside tab 90 on the locking marker element 70. A fusion line 126 defines an interface between the neck 122 and knob 124 and the rounded space 62 and gap 63 of the receiver 60. As with the fusion line 96, the fusion line 126 provides a region where the outside tab 120 can be secured to the receiver 60 either by melting of the knob 124 such as by heat from a laser or by brazing or other attachment techniques.

Figure 12:
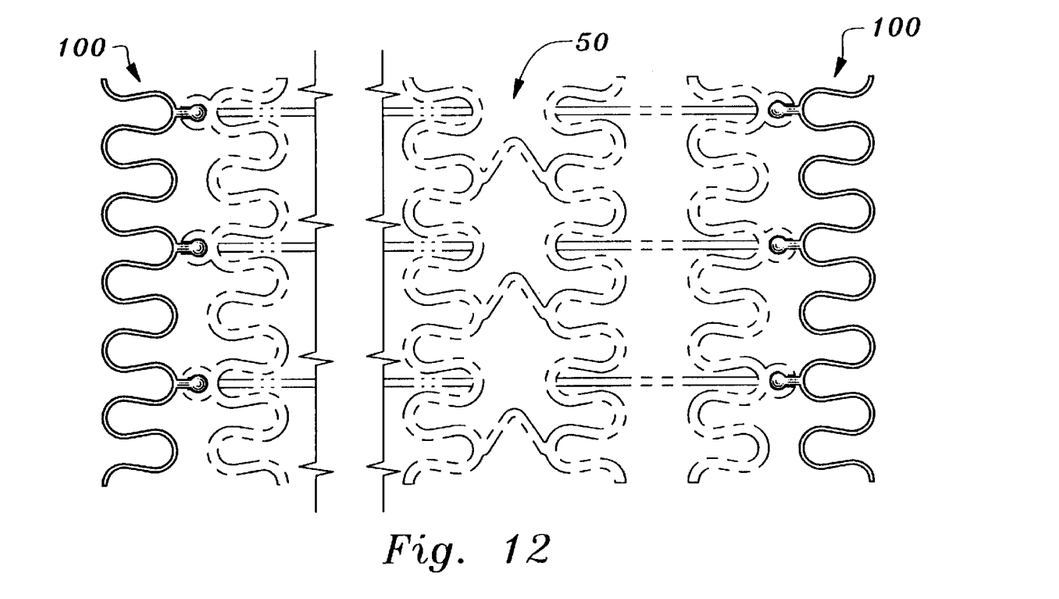
FIG. 12 is a cylindrical projection of the prepped stent of FIG. 7 with two extended marker elements attached to ends of the prepped stent. Portions of the prepped stent are shown with broken lines indicating that the prepped stent is formed of non-radiopaque material. Portions of the extended marker elements are shown with a solid lines representing that the extended marker elements are formed from radiopaque material and would exhibit enhanced visibility when viewed with a medical imaging device.
Figure 13:
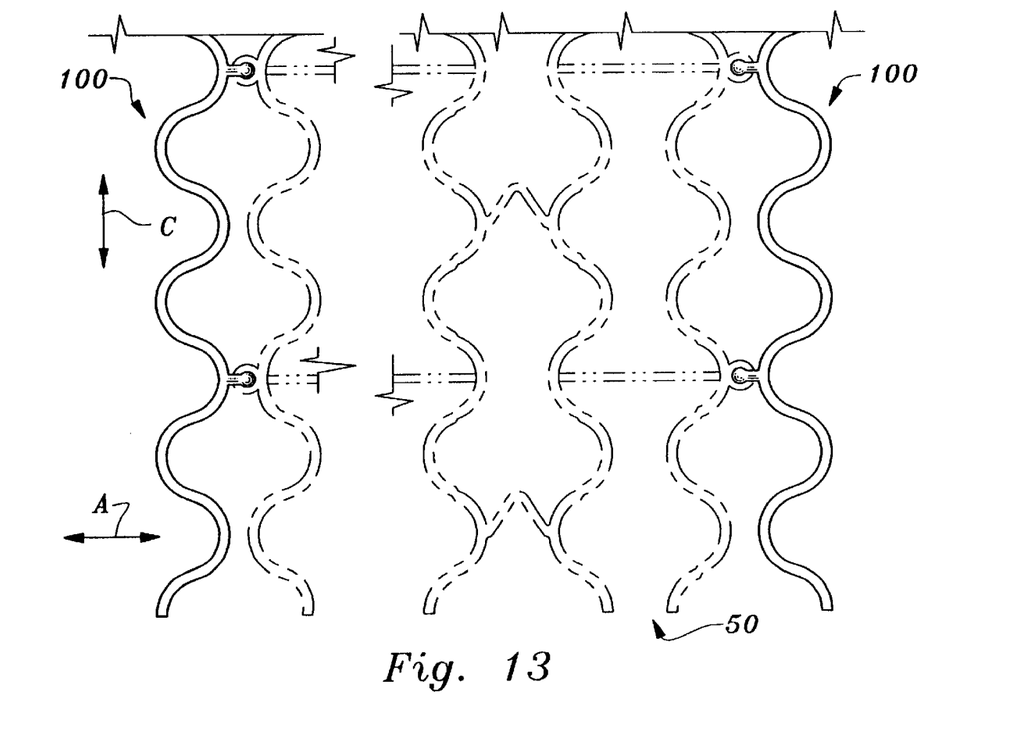
FIG. 13 is a cylindrical projection of a portion of that which is shown in FIG. 12 revealing the configuration of the prepped stent and extended marker elements when the prepped stent and extended marker elements are radially expanded.
Figure 14:
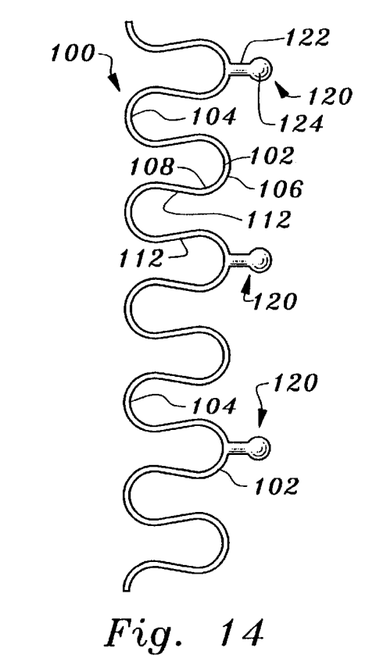
FIG. 14 is a cylindrical projection of the extended marker element before its attachment to the prepped stent.
Figure 15:
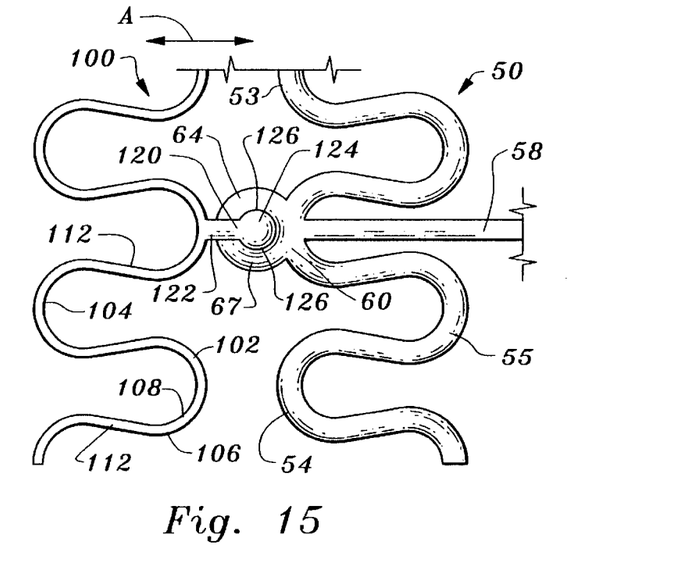
FIG. 15 is a cylindrical projection of a portion of that which is shown in FIG. 12 revealing details of the attachment of the extended marker element of FIG. 14 to the prepped stent of FIG. 7.
Figure 16:
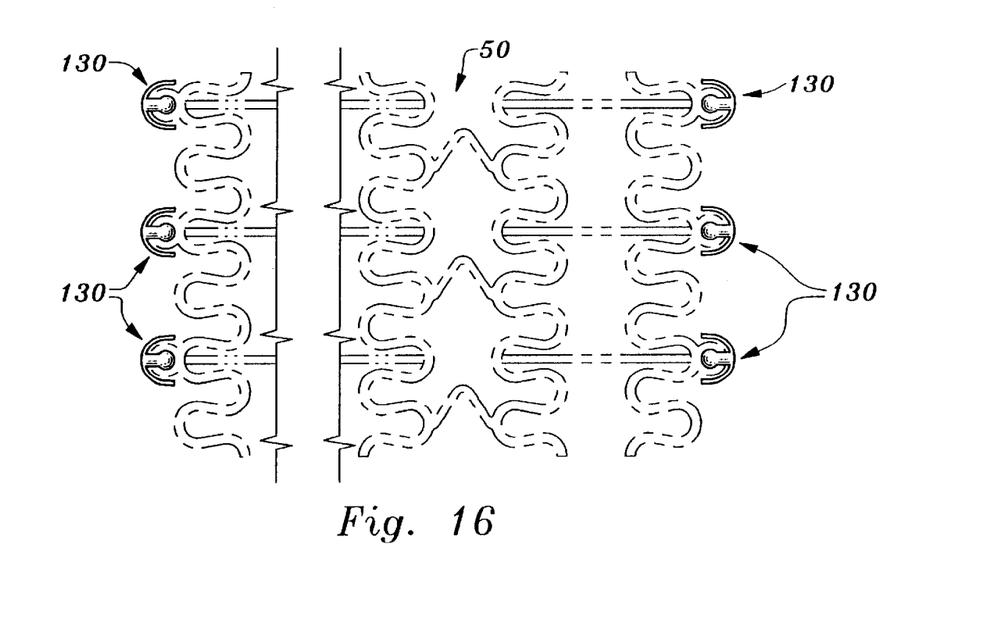
FIG. 16 is a cylindrical projection of the prepped stent of FIG. 7 with multiple cap marker elements attached to ends of the prepped stent. Portions of the prepped stent are shown with broken lines indicating that the prepped stent is formed from non-radiopaque material. Portions of the cap marker elements are shown with solid lines indicating that they are formed from radiopaque material and would exhibit enhanced visibility when viewed with a medical imaging device.
Figure 17:
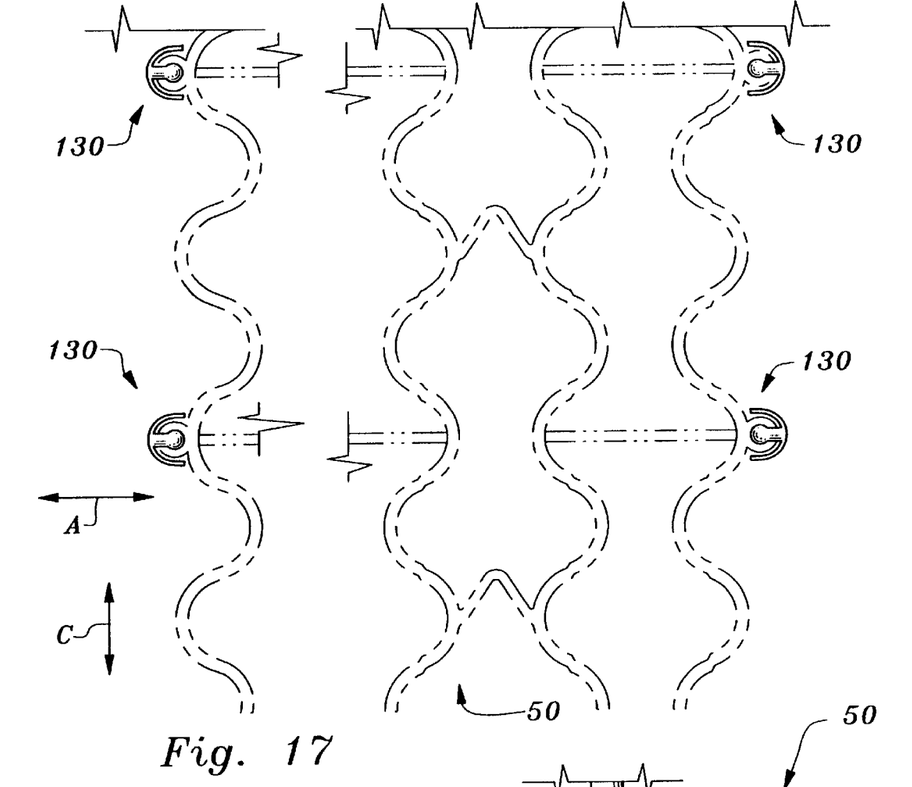
FIG. 17 is a cylindrical projection of a portion of that which is shown in FIG. 16 revealing the configuration of the prepped stent and capped marker elements when the prepped stent is radially expanded.
Figure 18:
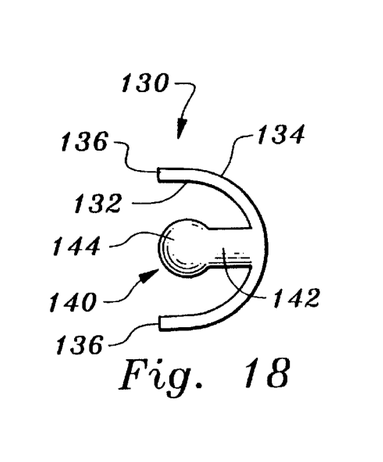
FIG. 18 is a top plan view of a single cap marker element.
Figure 19:
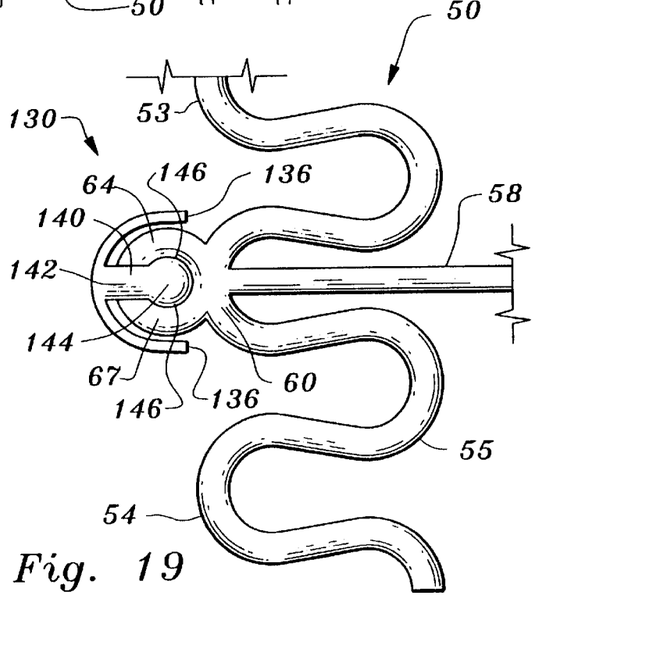
FIG. 19 is a cylindrical projection of a portion of that which is shown in FIG. 16 revealing details of the attachment of the cap marker element of FIG. 18 to the prepped stent of FIG. 7.

As shown in FIGS. 12 and 13, the extended marker elements 100 do not interfere with radial expansion of the prepped stent 50 and circumferential elongation, along arrow C. Rather, the extended marker elements 100 expand radially along with the prepped stent 50. The extended marker elements 100 do not merely provide enhanced visibility for the stent 50 when viewed through a medical imaging device. Rather they also provide support for the body lumen in which the stent 50 and extended marker elements 100 are together implanted.

With particular reference to FIGS. 16–19, details of a cap marker element 130 for attachment to the receivers 60 of the prepped stent 50 are provided. Each cap marker element 130 is analogous to the locking marker element 70 except that rather than being a continuous circumferential element, each cap marker element 130 is discontinuous and only resides in a region directly adjacent the receiver 60. When cap marker elements 130 are attached to receivers 60 on the prepped stent 50, discreet locations of enhanced radiopacity would be provided, rather than a continuous line of radiopaque material circumferentially surrounding the stent 50.

Each cap marker element 130 includes a concave side 132 configured to face the receiver 60 and a convex side 134 opposite the concave side 132. The cap marker element 130 has ends 136 where the cap marker element 130 terminates. The ends 136 are preferably sufficiently close to other portions of each cap marker element 130 that the cap marker element 130 does not extend away from a region in which the receiver 60 is located.

The convex side 134 of each cap marker element 130 includes a cap tab 140 extending axially, along arrow A, away from the convex side 134. Each cap tab 140 includes a neck 142 with a knob 144 at an end of the neck 142 opposite the convex side 134. A fusion line 146 surrounds the knob 144. Thus, the cap tab 140 has a similar contour to the outside tab 120 and inside tab 90. The cap tab 140 and cap marker element 130 are attached to the receiver 60 and prepped stent 50 in a similar manner to attachment mechanisms discussed above with respect to the inside tab 90 of the locking marker element 70 and the outside tab 120 of the extended marker element 100.

In use and operation, and with particular reference to FIG. 1, details of the operation and use of the stent 10, 50 featuring radiopaque markers 20, 70, 100, 130 are described. Initially, a stent 10 or prepped stent 50 is provided having the desired cylindrical configuration depending on the particular needs of the surgical procedure to be performed. The radiopaque marker element is selected for attachment to each of the ends 2, 4 of the stent 10, 50 so that the ends 2, 4 can be clearly visualized with a medical imaging device, such as a fluoroscope. Such enhanced visibility is beneficial during the implantation procedure to precisely determine the location of the stent 10, 50 both before and after radial expansion thereof and after implantation of the stent 10, 50 to verify the correct positioning of the stent 10, 50 on a periodic basis after the surgical procedure.

A marker element 20, 70, 100, 130 is selected depending on the desired configuration for the stent 10, 50 and the particular needs for which the stent 10, 50 is to be utilized. If the stent 10 without any modification to the ends 2, 4 is utilized, it is preferable that the circumferential marker elements 20 are utilized. First, circumferential marker elements 20 are oriented adjacent the ends 2, 4 of the stent 10. An attachment means, such as a series of braze points 40 can then be utilized to secure the circumferential marker elements 20 to the first end 2, and second end 4 of the stent 10. The stent 10 can then be utilized in the surgical procedure as is known in the art.

If the prepped stent 50 is to be provided with radiopaque markers, a locking marker element 70 can be selected which remains directly adjacent ends of the prepped stent 50. Other choices include the extended marker element 100 which increases an axial length of the prepped stent 50 or cap marker elements 130 which attach at discreet locations to each receiver 60 on the prepped stent 50. Once the appropriate marker element 20, 70, 100, 130 is selected and located adjacent ends of the prepped stent 50, an appropriate attachment means, such as those discussed above is utilized to secure the marker element 20, 70, 100, 130 to the receiver 60 of the prepped stent 50. Once the marker element 20, 70, 100, 130 is attached to the prepped stent 50, the prepped stent 50 is configured for use in a surgical procedure.

Having thus described the invention through a series of preferred embodiments, it should be apparent that other modifications to this invention could be resorted to without departing from the scope of this invention. These preferred embodiments are described not to limit the scope of the claims included herein but rather to provide examples of the implementation of the invention disclosed herein. While the preferred embodiments have disclosed two marker elements for each stent with one marker element adjacent each end of each stent, it is understood that a single marker element could be attached to a single end of the stent should enhanced visibility of only one end of the stent be considered desireable. Additionally, different marker elements 20, 70, 100, 130 could be utilized together on a single stent 10, 50. Additionally, it is understood that the marker elements could be formed from any material having the desired characteristics for enhanced visibility when viewed with a medical imaging device. When various different medical imaging devices are utilized, the materials forming the marker elements 20, 70, 100, 130 can be appropriately adjusted to provide the desired enhanced visibility feature.

What is claimed is:

1. A radiopaque radially expandable stent for surgical implantation into a body lumen, such as an artery, said stent having a generally cylindrical contour both before and after expansion thereof, said stent further comprising in combination:

a stent frame having a first stent end and a second stent end opposite said first stent end;

at least two marker members each being homogeneous and having a preformed size and shape corresponding to an associated portion of the stent frame before being attached thereto, including a first marker member and a second marker member, each marker member formed from a material which is radiopaque having a radiopacity than the stent frame; and said first marker member being attached directly to said stent frame at said first stent end and said second marker member attached directly to said stent frame at said second stent end, said first and second marker members extending at least partially beyond said first and second stent ends and being attached at least at two circumferentially spaced apart locations about respective ones of said first and second stent ends, whereby the maximum extent of the stent frame can be viewed with a fluoroscope.

2. The stent of claim 1 wherein said attachments include braze points where said marker members are brazed to said ends to which said marker members are attached.

3. The stent of claim 1 wherein said at least two marker members are circumferential in form extending completely around said cylindrical contour of said stent frame, said marker members having a diameter similar to a diameter of said stent frame and being radially expandable.

4. The stent of claim 3 wherein said first marker member and said second marker member have a marker contour which matches an end contour of said first end and said second end of said stent frame, said marker members located adjacent said ends, said end contour including wave-like undulations including a series of crests and troughs, said marker members located adjacent to and following said crests and troughs of said end contour of said first end and said second end as said marker members extend circumferentially around said cylindrical contour of said stent frame.

5. A radiopaque marker member for a generally cylindrical, radially expandable surgical stent frame configured to be implanted into a body lumen, the stent frame having a central axis, a radius, a first generally circular end and a second generally circular end opposite the first generally circular end, said radiopaque marker comprising in combination:

at least one marker member being homogeneous and having a preformed size and shape corresponding to an associated portion of the stent frame before being attached thereto, said circumferential marker member formed of a marker material which has a greater radiopacity than a stent material forming other portions of the stent frame;

said circumferential marker member being generally circular and having a substantially constant radius from an axial center of said circumferential marker element and being substantially equal to the radius of the stent frame; and means to attach said circumferential marker member to one of the ends of the stent frame such that said axial center located upon the central axis of the stent frame, whereby the maximum extent of the stent frame can be viewed with a fluoroscope.

6. The radiopaque marker member of claim 5 wherein said circumferential marker member extends in a continuous fashion entirely around said axial center.

7. The radiopaque marker member of claim 5 wherein a first circumferential marker member is adapted to be attached through said attachment means to the first generally circular end of the stent frame and a second circumferential marker member similar to said first circumferential marker member is adapted to be attached through said attachment means to the second generally circular end of the stent frame.

8. The radiopaque marker member of claim 5 wherein said constant radius of said circumferential marker member is radially expandable from a lesser amount to a greater amount when the surgical stent frame is similarly radially expanded from a lesser radius to a greater radius.

9. The radiopaque marker member of claim 8 wherein said radial expansion means of said circumferential marker member includes said circumferential marker member is formed in an undulating pattern with a series of troughs and crests therein, said material forming said circumferential marker member having sufficient flexibility to allow a distance between adjacent said crests and adjacent said troughs in said circumferential marker member to be extended away from each other, increasing a circumferential length of said circumferential marker member and increasing said constant radius of said circumferential marker member.

10. The radiopaque marker member of claim 8, wherein radial expansion of said circumferential marker member is matched with radial expansion of the surgical stent frame to which said circumferential marker member is attached through said attachment means.

11. The radiopaque marker element member of claim 5 wherein said circumferential marker member extends beyond the end of the stent frame to which said circumferential marker member is attached.

12. A radially expandable surgical stent featuring separate radiopaque marker members joined thereto, said stent further comprising in combination:

a stent frame having a first end and a second end opposite said first end and connected to said first end by a plurality of stent elements arranged in a generally cylindrical form together forming said stent frame, said stent elements being radially expandable from a first diameter to a second diameter;

at least one marker member being homogeneous and having a preformed size and shape corresponding to an associated portion of the stent frame before being attached thereto, said marker member formed from a material which is radiopaque; and a means joining said marker member directly to said stent frame at one of said ends of said stent such that said marker member extends at least partially beyond said stent end and is joined at least at two circumferentially spaced apart locations about said stent end, whereby the maximum extent of the stent frame at said stent end can be viewed with a fluoroscope.

13. The surgical stent of claim 12 wherein said joining means includes a receiver on one of said stent frame and said marker member and a tab on another of said stent frame said marker member, said receiver being complementary to said tab to lockably receive said tab there into.

14. The surgical stent of claim 13 wherein said tab includes a neck and a knob connected to said neck, said knob having a greater width than said neck, said receiver having a rounded space and a gap adjacent said rounded space, said rounded space having a width greater than a width of said gap, said knob of said tab having a greater width than said gap of said receiver, such that when said knob of said tab is located within said rounded space of said receiver, said tab cannot be removed from said receiver by passing said knob of said tab through said gap of said receiver.

15. The surgical stent of claim 13 wherein said tab and said receiver are at least partially melted together in a manner securing said marker member to said stent frame.

16. The surgical stent of claim 15 wherein said at least on marker member is joined through said joining means to said first end of said stent frame and a second marker member is attached through said joining means to said second end of said stent frame, said first end of said stent frame having at least one receiver extending therefrom, said second end of said stent frame having at least one receiver extending therefrom, said at least one marker member having at least one tab thereon, and said second marker member having at least one tab thereon, each said marker member having an undulating contour with crests and troughs opposite said crests, said tab extending from one of said crests.

17. The surgical stent of claim 12, wherein said plurality of stent elements include at least two circumferential elements extending entirely around said generally cylindrical form of said stent frame and defining said first end of said stent frame and said second end of said stent frame, said circumferential elements having end contours including a series of troughs and crests alternating as said circumferential elements extend around said cylindrical form of said stent frame, said at least one marker member being substantially cylindrical and having a marker contour essentially identical in shape to said end contour of said circumferential elements forming said first end of said stent frame.

18. The surgical stent of claim 12, wherein said marker member comprises a plurality of discrete members each joined to said stent end at a respective location about the circumference thereof.

19. The stent of claim 1, wherein said at least two marker members comprise a plurality of discrete first marker members each joined to said first stent end at a respective location about the circumference thereof, and a plurality of discrete second marker members each joined to said second stent end at a respective location about the circumference thereof.

20. The stent of claim 19, wherein each of said discrete first and second marker members is shaped convex in a direction facing away from a respective said stent end.

\* \* \* \* \*